US005520679A

United States Patent [19]
Lin

[11] Patent Number: 5,520,679
[45] Date of Patent: May 28, 1996

[54] OPHTHALMIC SURGERY METHOD USING NON-CONTACT SCANNING LASER

[75] Inventor: J. T. Lin, Winter Springs, Fla.

[73] Assignee: LaserSight, Inc., Orlando, Fla.

[21] Appl. No.: 218,319

[22] Filed: Mar. 25, 1994

Related U.S. Application Data

[63] Continuation-in-part of Ser. No. 985,617, Dec. 3, 1992, abandoned.

[51] Int. Cl.$^6$ .................................................... A61N 5/02
[52] U.S. Cl. ................................. 606/5; 606/4; 128/898
[58] Field of Search ............................. 606/3–6, 10–12; 128/898

[56] References Cited

U.S. PATENT DOCUMENTS

| 4,718,418 | 1/1988 | L'Esperance, Jr. | 606/5 |
| 4,729,372 | 3/1988 | L'Esperance, Jr. | 606/5 |

Primary Examiner—Angela D. Sykes
Assistant Examiner—Michael Peffley
Attorney, Agent, or Firm—William M. Hobby, III

[57] ABSTRACT

A refractive laser surgery process is disclosed for using compact, low-cost ophthalmic laser systems which have computer-controlled scanning with a non-contact delivery device for both photo-ablation and photo-coagulation in corneal reshaping. The basic laser systems may include flash-lamp and diode pumped UV solid state lasers (193–215 nm), compact excimer laser (193 nm), free-running Er:glass (1.54 microns), Ho:YAG (2.1 microns), Q-switched Er:YAG (2.94 microns), and tunable IR lasers, (750–1100) nm and (2.5–3.2) microns. The advantages of the non-contact, scanning device used in the process over other prior art lasers include being safer, reduced cost, more compact and more precise and with greater flexibility. The theory of beam overlap and of ablation rate and coagulation patterns is also disclosed for system parameters. Lasers are selected with energy of (0.01–10) mJ, repetition rate of (1–10,000), pulse duration of 0.01 nanoseconds to a few hundreds of microseconds, and with spot size of (0.05–2) mm for use with refractive laser surgery.

23 Claims, 5 Drawing Sheets

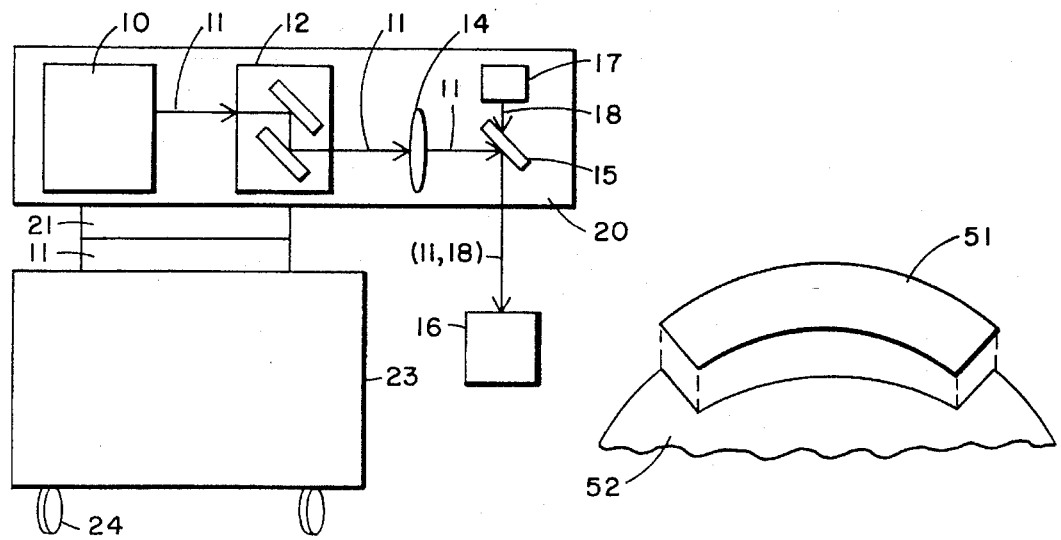
FIG. 1
FIG. 5A
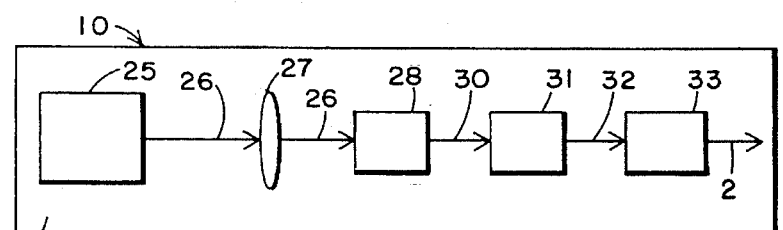
FIG. 2
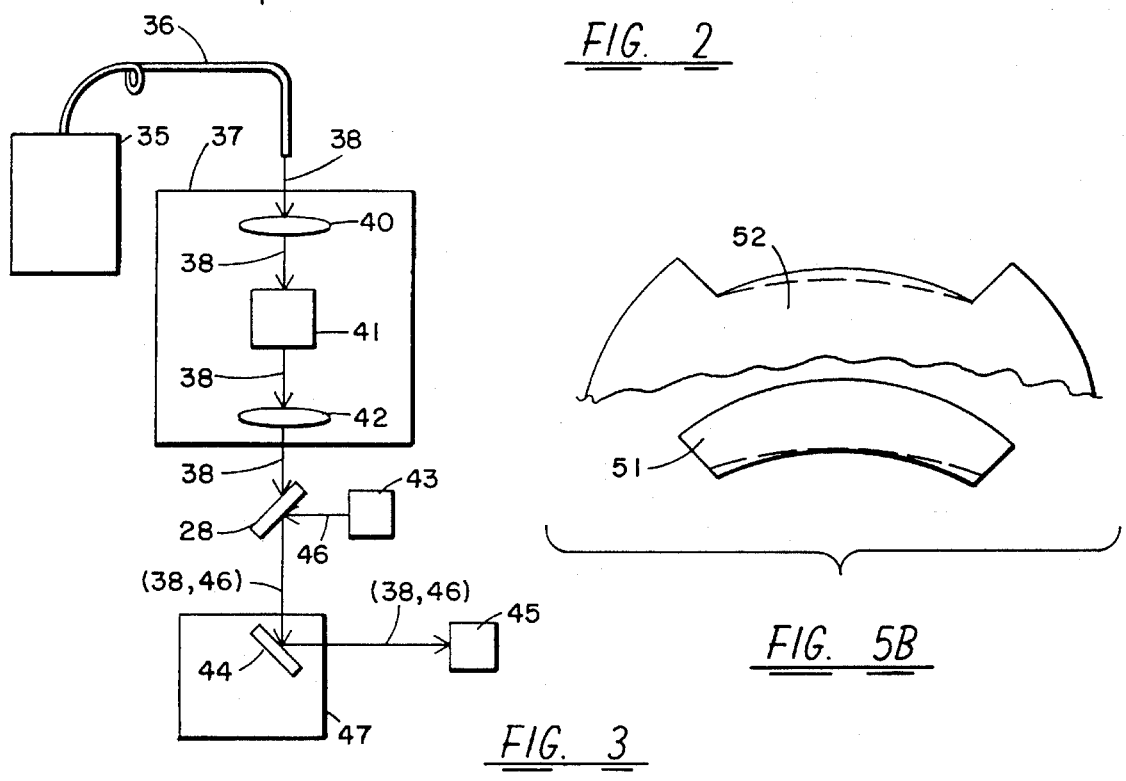
FIG. 3
FIG. 5B

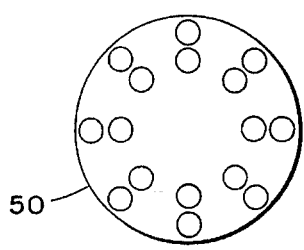
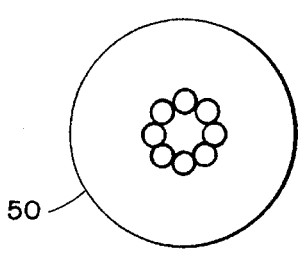
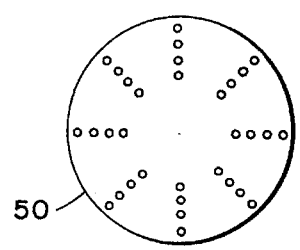
FIG. 4A　　　　　FIG. 4B　　　　　FIG. 4C
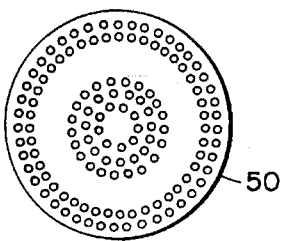
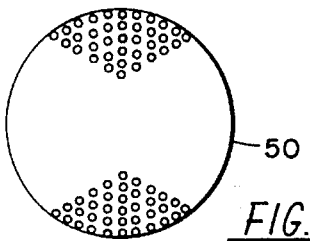
FIG. 4D　　　　　FIG. 4E
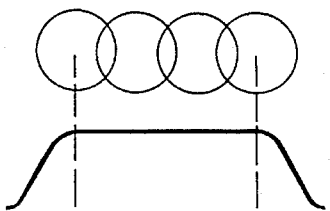
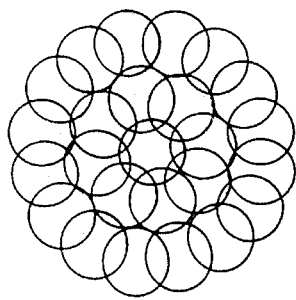
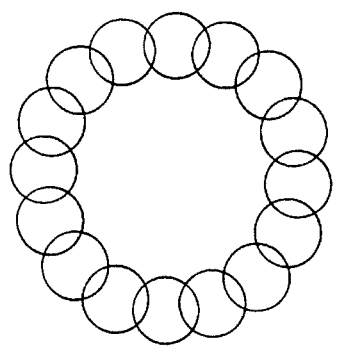
FIG. 6A　　　　　FIG. 6B　　　　　FIG. 6C
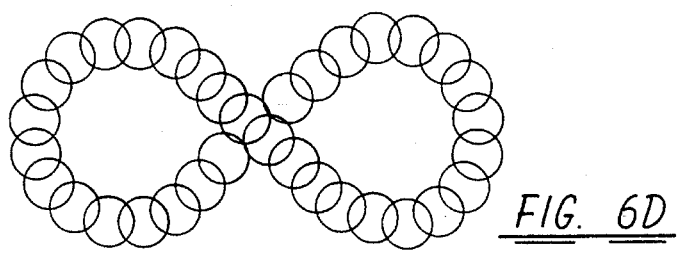
FIG. 6D
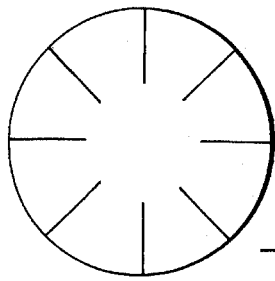
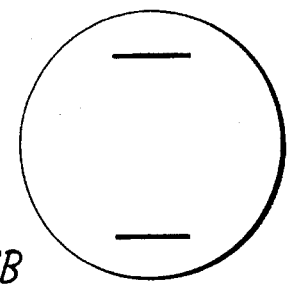
FIG. 7A　　　　　FIG. 7B 5,520,679

OPHTHALMIC SURGERY METHOD USING NON-CONTACT SCANNING LASER

This application is a continuation-in-part application of Ser. No. 07/985,617, filed Dec. 3, 1992 now abandoned.

BACKGROUND OF THE INVENTION

1. Field of the Invention

The present invention relates to laser ophthalmic surgery using a compact, low-cost, low-power laser system with a computer-controlled, non-contact process and corneal topography to perform corneal reshaping using either surface ablation or thermal coagulation.

2. Prior Art

Various lasers have been used for ophthalmic applications including the treatments of glaucoma, cataract and refractive surgery. For non-refractive treatments (glaucoma and cataract), suitable laser wavelengths are in the ranges of visible to near infrared. They include: Nd:YAG (1064 nm), doubled-YAG (532 nm), argon (488, 514 nm), krypton (568, 647 nm), semiconductor lasers (630–690 nm and 780–860 nm) and tunable dye lasers (577–630 nm). For refractive surgeries (or corneal reshaping), ultraviolet (UV) lasers (excimer at 193 nm and fifth-harmonic of Nd:YAG at 213 nm) have been used for large area surface corneal ablation in a process called photorefractive keratectomy (PRK). Corneal reshaping may also be performed by laser thermal coagulation currently conducted with Ho:YAG lasers using a fiber-coupled, contact-type process. However, the existing ophthalmic lasers as above described have one or more of the following limitations and disadvantages: high cost due to the high-power requirement in UV lasers for photorefractive keratectomy; large size and weight; high maintenance cost and gas cost (for excimer laser), and high fiber-cost for contact-type laser coagulation.

In light of the above, it is an object of the present invention to provide ophthalmic laser systems which offer the advantages of: low-cost, reduced size and weight, reliability, easy-operation and reduced maintenance. Another object of this invention is to provide a computer-controlled scanning device which enables use of a low-cost, low-energy laser for photorefractive keratectomy currently performed only by high-power UV lasers.

It is yet another object of the present invention to provide a refractive laser system which is compact, portable and insensitive to environmental conditions (such as vibration and temperature). This portable system may also be used for a mobile clinical center where the laser is transported by a van. It is yet another objective of the present invention to provide a non-contact process for corneal reshaping using laser thermal coagulation, where predetermined corneal correction patterns are conducted for both spherical and astigmatic changes of the corneal optical power.

The prior U.S. Pat. No. 4,784,135 to Blum, et al. and assigned to IBM teaches the first use of far ultraviolet irradiation of a biological layer to cause ablative photodecomposition. This patent teaches that using a laser beam housing a wavelength of 193 nm and an energy level of much greater than 10 mJ/cm$^2$/pulse can be used to photoablate corneal tissue without the build up of excess heat. The present invention on the other hand uses a process that allows the use of energy levels of less than 10 mJ/pulse in a process that still allows photoablation.

There are several prior art U.S. Patents relating to refractive surgery, or photorefractive keratectomy. A UV solid-state fifth-harmonic of Nd:YAG (or Nd:YLF) laser at 213 nm (or 210 nm), is disclosed in U.S. Pat. No. 5,144,630 by the inventor, J. T. Lin. U.S. Pat. No. 4,784,135 suggests the use of a UV laser with wavelengths less than 200 nm, in particular Argon Fluoride (ArF) laser at 193 nm, for non-thermal photoablation process in organic tissue. Devices for beam delivery and methods of corneal reshaping are disclosed in U.S. Pat. No. 4,838,266 using energy attenuator, and U.S. Pat. No. 5,019,074 using an erodible mask. Techniques for corneal reshaping by varying the size of the exposed region by iris or rotating disk are discussed in Marshall et al, "Photoablative Reprofiling of the Cornea Using an Excimer Laser: Photorefractive Keratectomy" Vol. 1, Lasers in Ophthalmology, pp. 21–48 (1986). Tangential corneal surface ablation using ArF excimer laser or harmonics of Nd:YAG laser (at 532 and 266 nm) is disclosed in U.S. Pat. No. 5,102,409.

This prior art however requires high UV energy of (100–300 mJ) per pulse from the laser cavity or (30–40) mJ per pulse delivered onto the corneal surface, where large area corneal ablation using a beam spot size of about (4–6) mm which gives an energy density of (120–200) mJ/cm$^2$. Moreover, the prior art Argon Fluoride excimer lasers operate at a repetition rate of (5–15) Hz and also limit the practical use of the tangential ablation concept which takes at least (5–10) minutes for a –5 diopter corneal correction in a 5-mm optical zone. The high energy requirement of the currently used Argon Fluoride excimer laser suffers the problems of: high-cost (in system, erodible mask and gas cost), high-maintenance cost, large size/weight and system are sensitive to environmental conditions (such as temperature and moisture).

The prior L'Esperance patent, U.S. Pat. No. 4,665,913, disclosed the method of a scanning laser for corneal reshaping. The proposed concept of this prior art, however, had never been demonstrated to be practical or to achieve the desired clinical requirement of smooth ablation of the corneal surface. This prior art is not practically useful and had not ever been demonstrated to be real because of the conditions in the art. A high-power laser of (100–200 mJ) is required in the prior art in order to obtain a useful beam with a substantially square spot size of 0.5×0.5 mm (see prior art, Col. 3, line 65 and Col. 4, lines 1–14) due to the low efficiency of obtaining such a beam, and which further requires a substantially uniform density (see Col. 13, line 30 and Col. 15, line 25). To achieve myopic correction, for example, the prior art (Col. 13, lines 61–66 and Col. 15 lines 60–65) proposes a smooth laser density increase with increasing scanning radius under the condition that a substantially uniform density of the scanning beam is required for a substantially uniform scan area (Col. 15, lines 20–28 of L'Esperance). Furthermore, L'Esperance teaches (Col. 4, lines 40–50) that a depth of 0.35 mm in an area of 6 mm diameter might be achieved in about 15 seconds when a beam spot of 0.5×0.5 mm is used and each pulse ablated 14 microns. The prior art proposes the method of having individual square beams (0.5×0.5 mm) scan to the fashion of exact matching of the square boundaries to cover the area of 6 mm, where the overlap among these individual beams should be avoided, otherwise excessive ablation near the boundaries of each 0.5×0.5 mm spot causes ridges. This is also part of the reason that the prior art requires a substantially square section of the individual beam with a substantially uniform density.

The L'Esperance U.S. Pat. No. 4,665,913 requires a complex apparatus to select a section of the beam which is substantially uniform in density within a substantially square spot "dot". The overall efficiency would be less than 10% from the output of the laser window to the corneal surface and requires, where a high power (at least 100 mJ) excimer laser than will be required than the Blum, et al. patent. It is almost impossible to match exactly the boundary of each square beam to achieve a substantially uniform scanned area even if each individual beam is perfectly uniform and square in shape and the smooth increase of the radius of scanned areas to obtain, for example, a myopic correction profile, would still be almost impossible to achieve for an overall smooth corneal surface. The successive sweep of the scan areas would always leave ridges between these sweeps. It should also be noticed that in L'Esperance's patent (Col. 18, lines 10–28) uses overlaps between each of the scanned areas to obtain the desired ablation profiles of myopic (or other) corrections. However, the ridges between each of the successive ablated areas are very difficult to avoid if within each scanned area the ablated profiles are not substantially uniform. In fact, one should expect a very rough surface on these ablated areas in addition to the regular ridges between each overlapped zones. One of the problems found in these teachings is that each required individual ablated area be substantially uniform and in a round or square shape, which is very difficult to achieve even if a perfectly uniform, square portion of a fundamental beam is produced using a complex apparatus for beam reshaping and having the high initial power.

It is not clear that L'Esperance has found a suitable scanning method or an effective method of selecting a perfect beam (with uniform density and well-defined shape) which would overcome the above-described difficulties and make the proposed teaching become practical in cost and design for any clinical uses. In fact, L'Esperance's scanning method has also been challenged by another prior art of Muller, U.S. Pat. No. 4,856,513, where the difficulties and problems of L'Esperance's teachings are discussed (see Col. 2, lines 1–40 of Muller's patent).

It is therefore a further object of the present invention to provide a method and apparatus for corneal reshaping by using software-driven new scanning patterns which do not require substantially uniform density or a specific spot shape. Contrary to L'Esperance's teachings, which suggest that there should be a perfect boundary match among each square beams and that excessive overlap should be avoided, the present invention proposes that a large portion (50%–80%) of overlap among the individual beams is necessary in order to achieve uniform ablated areas and a smooth profile without ridges. Furthermore, a low-power UV laser (0.1–2 mJ on corneal surface) at its bare-beam (having typically a 3-lop profile) without any beam reshaping is sufficient to achieve a smooth ablation surface based on the method proposed in the present invention, where computer-controlled beam overlap and orientation are employed. In addition to the surface quality problems, it is also impossible for L'Esperance to achieve any meaningful clinical results using his proposed techniques based on the present low-energy laser of (2–4) mJ from the output laser window and (0.1–2) mJ on corneal surface.

Therefore, another object of the present invention is to provide a new method of beam scanning which combines beam overlap and orientation for a random beam density distribution on the ablated corneal surface such that the individual beam profiles are not critical, where the focused beam (spot size of 0.1–1.2 mm) uses very low energy (0.1–2 mJ) and at its bare-profile is delivered onto the corneal surface in an averaged fashion. Uniform, near flat-top ablated areas of (1–9 mm in diameter) can be performed by the nonuniform starting-beam, but only when a set of specific predetermined overlap and orientation parameters are used. Portions of the theoretical background was published by the inventor, J. T. Lin, in SPIE Pro. vol 1644, Ophthalmic Technologies II (1991), p.p. 266–275.

One of the essential feature of the present invention for the photorefractive keratectomy process is to use a scanning device in a laser system which has high repetition rates, 50 to 50,000 Hz, but requires less energy, ranging between 0.05–10 mJ per pulse, or about 10 to 100 times less than that of the prior art. This new concept enables one to make the refractive lasers at a lower cost, smaller size and with less weight (by a factor of 5–10) than that of prior art lasers. Furthermore, these compact lasers of the present invention are portable and suitable for mobile clinical uses. To achieve beam uniformity and fast refractive surgery (30 to 60 seconds), a mathematical model of the beam overlap and ablation speed is also disclosed in the present invention.

For the laser thermo-keratoplasty (LTK) process, the prior art uses fiber-coupled contact-type procedure which involves the following drawbacks: (i) slow processing speed (typically a few minutes to perform eight-spot coagulation) which causes the non-uniform collagen shrinkage zone; (ii) circular coagulation zone which limits the procedure only for spherical type correction such as hyperopia; and (iii) the contact fiber-tip must be replaced in each procedure.

In the present invention, a computer-controlled scanning device is able to perform the laser thermokeratoplasty procedure under a non-contact mode and conduct the procedure many times faster than that of the prior contact-procedure and without cost for a fiber-tip replacement. Furthermore the coagulation patterns can be computer predetermined for specific applications in both spherical and astigmatic corrections. The flexible scanning patterns will also offer uniform and predictable collagen shrinkage.

For ophthalmic applications, it is another objective of the present invention to include but not limited to photorefractive keratectomy, laser thermokeratoplasty, epikeratoplasty, intrastroma photokeratectomy (IPK), phototherapeutic keratectomy (PTK), and laser-assisted keratomileusis (LAK).

SUMMARY OF THE INVENTION

The preferred embodiments of the basic ophthalmic surgery method uses a laser system for the ophthalmic surgery process, including: (1) a diode-pumped solid-state lasers of Nd:YAG or Nd:YLF which is frequency-converted by nonlinear crystals of KTP (potassium titanyl phosphate), LBO (lithium triborate), KNbO3 (potassium niobate) and BBO (beta barium borate) into the fifth-harmonic at wavelength of 213 nm or 210 nm with energy of 0.01 to 5.0 mJ; (2) a compact, low-cost, low-power (energy of 1 to 10 mJ per pulse) argon fluoride excimer laser at 193 nm; (3) a frequency-converted Alexandite or Li:SAF or diode. lasers at (193–220) nm; (4) a compact, low-cost, Q-switched Er:YAG laser at 2.94 microns; (5) a free-running Ho:YAG (at 2.1 microns) or Er:glass (at 1.54 microns) or diode laser (1.9–2.5 microns); (6) ultrashort pulse IR laser (750–1100 nm) and (7) mid-IR (2.5–3.2 microns) laser generated from optical parametric oscillation.

According to one aspect of the present invention, the above-described basic lasers includes UV-lasers (193–215 nm) and IR-laser (1.5–3.2 microns) which are focused into a spot size of (0.05–2) mm in diameter, where laser energy per pulse of (0.01–10) mJ is sufficient to achieve the photo-ablation threshold (PAT) energy density of 50 to 600 mJ/cm$^2$ depending upon the laser parameters (wavelengths and pulse duration) and tissue properties (absorption and scattering). The prior art excimer laser uses large beam spot ablation (4–6 mm) and require much higher laser energy (100–300 mJ) than the low-power lasers presented in this invention. In the present invention, a scanning, non-contact device is used to control the low-power laser for corneal diopter change, whereas diaphragms or masks are used in the high-power, high-cost excimer lasers, and contact, fiber-tip is used in the photo-coagulation procedure.

In another aspect of the present invention, a mathematical model is presented according to the optimal beam overlap for beam uniformity and fast procedure and scanning patterns for refractive corrections of myopia, hyperopia and astigmatism. For high-repetition lasers (50 to 5,000 Hz as proposed herein), refractive procedures may be completed in 20 to 60 seconds (depending on the diopter corrections) in the present invention, where scanning speed is only limited by the laser repetition rates.

A three-dimensional translation device (in X, Y and Z) is integrated into the above laser systems, where the laser heads are compact and light-weight and can be steered to the corneal center by the translation stages. The prior art high-powered excimer laser systems are stationary and require a motorized chair for corneal concentration. Beam steering and scanning is very difficult for these high-power, heavy-weight excimer lasers.

In yet another aspect of the present invention, a free-running Ho:YAG ( at 2.1 microns) or Er:glass (at 1.54 microns) or diode (1.9–3.2 microns) laser delivers a beam by a fiber waveguide and coupled to a scanning device for non-contact procedure for laser thermokeratoplasty (LTK), where optimal scanning patterns for corneal coagulation are performed for both spherical and astigmatic corrections.

In yet another aspect of the present invention, the above-described laser system provides an effective, low-cost tool for procedures of synthetic epikeratoplasty (SEK), where the artificial lens is sculpted with the laser to optimize lens curvature without causing problems of corneal haze and corrective regression. Real corneal tissues may also be sculpted and implanted by the above-described laser systems, a procedure known as laser myopic keratomileusis (MKM). Furthermore the UV and IR lasers disclosed in the present invention provide an effective tool for phototherapeutic keratectomy (PTK) which is currently conducted by high-power excimer lasers and the procedure conducted by diamond-knife called radial keratotomy (RK). This procedure conducted by UV or IR lasers is called laser radial keratotomy (LRK). The fundamental beam at 1064 or 1053 nm wavelength of the present invention may also be used for the intrastroma photorefractive keratectomy (IPK), where the laser beam is focused into the intrastroma area of the corneal and collagen tissue are disrupted.

The ophthalmic applications of the laser systems described in the present invention should include photorefractive keratectomy, phototherapeutic keratectomy, laser thermokeratoplasty, intrastroma photokeratectomy, synthetic epikeratoplasty, and laser radial keratotomy.

BRIEF DESCRIPTION OF THE DRAWINGS

FIG. 1 is a block diagram of computer-controlled laser system consisting of a laser, scanning device, power supply and the beam steering stage for ophthalmic applications;

FIG. 2 is a block diagram for the generation of ultraviolet wavelengths at 213 nm or 210 nm using nonlinear crystals in a diode-pumped system;

FIG. 3 is a block diagram of a computer-controlled refractive laser system of Ho:YAG or Er:glass or diode laser in a non-contact scanning mode for laser thermokeratoplasty;

FIGS. 4A through 4E shows computer-controlled scanning patterns for photo-coagulation in non-contact LTK procedures for both spherical and astigmatic corneal reshaping;

FIGS. 5A and 5B are procedures for laser-assisted myopic keratomileusis and hyperopic keratomileusis, where the reshaping can be performed either on the inner or outer part of the tissue;

FIGS. 6A through 6D show computer-controlled beam overlap and scanning patterns for myopic, hyperopic and astigmatic correction using UV (193–240 nm) or IR (0.7–3.2 microns) lasers;

FIGS. 7A and B laser radial keratectomy patterns (LRK) using laser excisions for myopia (radial-cut) and astigmatism (T-cut);

DETAILED DESCRIPTION OF THE PREFERRED EMBODIMENT

Figure 8A:
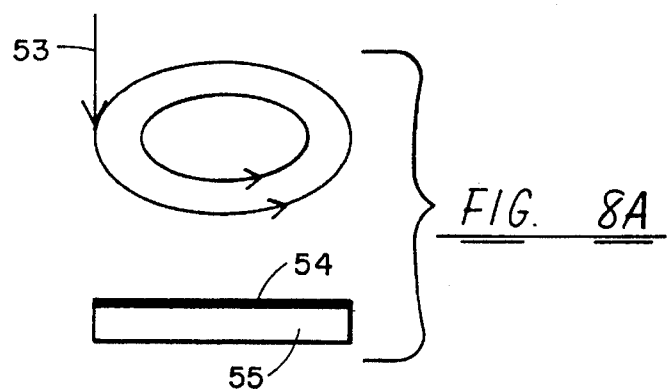
FIGS. 8A through 8D show ablation patterns for refractive correction using predetermined coatings on UV or IR grade windows.

The theoretical background of the present invention with regards to the beam overlap and ablation rate in photorefractive keratectomy, intrastroma photokeratectomy, synthetic epikeratoplasty, phototherapeutic keratectomy and myopic keratomileusis procedures described in the present invention is as follows.

Given a laser energy per pulse of m (in mJ), an intensity of I (in mJ/cm$^2$) may be achieved by focusing the beam into an area of A, where I=E/A. For corneal tissue ablation to occur requires the laser intensity (I) to be above the photoablation threshold (PAT), (60–120) mJ/cm$^2$ for UV-laser (193–215 nm) and (200–600) mJ/cm$^2$ for IR-laser (2.5–3.2 microns). Therefore it is always possible to tightly focus a laser beam and achieve the PAT value even for a low-energy laser (0.1–5) mJ. The drawback of using a low-energy, small-spot laser for large area ablation is that the operation time will be longer than that of a large-spot but high-power laser. However, time of operation may be shortened by using a high-repetition-rate laser (higher than 50 Hz). Small-spot, low-energy lasers for large area surface ablation would becomes practical only when a scanning device is used in a high-repetition-rate laser and only when uniform beam profile can be assured by the appropriate beam overlap. These two important issues are addressed in the present invention.

The overall operation rate (R) for a given diopter correction (D) is limited by the laser scanning rate (R1) which is in turn limited by the laser repetition rate. In addition, R is also proportional to the tissue ablation rate (RT) which is proportion to the laser intensity I (or energy density) at a given energy E.

The diopter change (D) in the case of myopia is related to the correction zone diameter (W) and the center ablation thickness (h0) and the ablation profile h(x) (at corneal position x) by:

$$h(x) = h0 + 1.32DX^2 \quad (1)$$

$$h0 = -0.3315DW^2 \quad (2)$$

In a scanning system as disclosed in the present invention, the number of ablation layers (M1) (without beam overlap) required for D-diopter correction is therefore related to the ablation thickness per pulse (T1), D, and W by $$M1 = h0/T1 = -0.3315DW^2/T1 \quad (3)$$

To include the overlap factor (F), F=2 for a 50% beam overlap scan and F=5 for 80% overlap, the required effective number of overlapped ablation layers is M1/F.

For a given ablation zone of W and laser focused spot area of A, one requires an effective single-layer scanning time (TS) of $FW^2/A$.

The total operation time(T) needed for h0 center ablation or D-diopter correction becomes $$T = (M1/F)(TS)DW^4/E \quad (4)$$

$$T = DW^4/E$$

Equation 4 gives us the scaling-law for operation time required (T), the laser energy (E), diopter change (D) and the ablation zone diameter (W). For a given laser energy per pulse of E, the overall operation rate (1/T) is independent to the laser intensity (I) and beam spot size (A). By increasing the laser average-power (P), defined by laser energy/pulse X repetition rate, more total energy may be delivered to the cornea per unit time. The average-power (P) is the key factor which actually determine the overall operation rate (or time) required to achieve the diopter change. By realizing that the scanning rate (1/TS) is proportional and synchronized to the laser repetition rate (RP), we are able to re-express Equation (4) as $$T = DW^4/P \quad (5).$$

It is important to note that given an average-power of P, the laser intensity must be above the photo-ablation threshold(PAT) by either beam focusing or increase the laser energy.

Based upon the above-described theory, some important features are: (i) CW lasers (either UV or IR) with low intensity normally can not cause photo-ablation since the energy density is lower than the PAT value; (ii) Lasers (UV or IR) at Q-switched or mode-locked mode and with pulse-duration shorter than 100 nanosecond will normally achieve the intensity above the PAT even at low-energy level of 0.05–5 mJ. In particular, picosecond lasers at high repetition rate is desirable where energy in the microjoule range would be sufficient. Moreover, the Q-switched short pulse lasers have smaller thermal damage than that of free-running lasers. The cost-effective refractive lasers are those which have high repetition rate (50 Hz and up) but operated at low-energy (0.05–5 mJ) and short pulse duration (0.001–20 nanoseconds). The preferred embodiments disclosed in the present invention as discussed in FIG. 1 are based upon this theory. Beam focusing and scanning are always required to achieve the PAT and smooth ablation profile. The individual beam profile in the scanning system is not as critical as that in prior art lasers which require a uniform overall profile within the large ablation zone of (4–6) mm. In laboratory tests, we have achieved a very smooth ablation profile with zone diameter up to 8 mm starting from a non-uniform focused beam profile which was randomly scanned over the ablation zone of (1–8) mm. Using overlap of (50–80)% of focused beam spot of (0.2–1.5) mm, and a typical number of pulses delivered to the corneal surface of 2,000–4,000, which assures a sufficient beam overlap for smooth profile and pulse to pulse energy fluctuation is not critical.

Referring to FIG. 1, a refractive laser system in accordance with the present invention comprises a basic laser 10 having UV (193–220 nm) or IR (0.7–3.2 microns) wavelength 11 coupled by a scanning device 12 having the beam from focusing optics 14 directed onto a reflecting mirror 15 into target 16 which target may be the cornea of an eye. An arming system 17 has a visible wavelength (from a laser diode or He—Ne laser) 18 adjusted to be collinear with the ablation beam 11 and defines the centration of the beam onto the cornea surface at normal incident. The basic laser head 20 is steered by a motorized stage for X and Y horizontal directions 21 and the vertical (height) direction 22 which assures the focusing beam spot size and the centration of the beam onto the cornea. The system has a computer controlled panel 23 and wheels 24 for portable uses. The target 16 includes a human cornea for applications of photorefractive keratectomy, phototherapeutic keratectomy and laser radial keratotomy (using the UV 193, 210, 213 nm or IR 2.9 microns beam focused on the corneal surface area) and intrastroma photokeratectomy (using the 1064 or 1053 or 1047 nm beam, or their second-harmonic, focused into the intrastroma area), and synthetic or real corneal tissues for applications of synthetic epikeratoplasty and myopic keratomileusis. The computer controlling panel 23 also provides the synchronization between the scanning gavo (galvanometer scanner) and the laser repetition rate. A commercially available galvanometer scanner made by General Scanning, Inc. is used in scanning the laser beam.

The laser systems described herein have been demonstrated using photorefractive keratectomy procedure with a diopter corrections up to −6 in PMMA plasty and −12 in corneal tissues. In the case of PMMA, we have also measured the diopters by a lensmeter with well-defined readings in the ranges of −1 to −12 diopters. This data provides the evidence of predictable diopter corrections using the laser systems of the present invention. Furthermore, minimal tissue thermal damage of 0.3–1.0 microns were measured by TEM (transmission electron microscopy). In measurements, a multi-zone (MZ) approach for high-diopter corrections (8–12) was used, where the center zone is 3 mm and the correction power decreases when the zone increases from 4 mm to 6 mm. This multi-zone approach reduces the overall ablation thickness and hence reduces the haze effect.

Still referring to FIG. 1, the basic laser 10, according to the present invention, includes a compact, optically-pumped (either flash-lamp or laser-diode pumped) lasers of Nd:YAG, Nd:YLF or the self-frequency-doubling crystal of NYAB (neodymium yttrium aluminum) with pulse duration of 0.05–20 nanoseconds and repetition rate of 1–10,000 Hz. It is known that this basic laser 10 is available using a standard Q-switch or mode-lock, where the UV wavelength at 209–213 nm may be achieved by the frequency conversion techniques using nonlinear crystals disclosed by the inventor in U.S. Pat. No. 5,144,630. The UV laser energy required for efficient ablation ranges from 0.01 mJ to 5 mJ. The basic laser also includes a compact, argon fluoride excimer laser (at 193 nm) with repetition rate of (1–1,000) Hz, energy per pulse of (0.5–10) mJ, pulse duration of (1–50) nanoseconds and a compact, Er:YAG laser (at 2.94 microns) with repetition rate of (1–200) Hz, energy per pulse of (50–500) mJ, pulse duration of (50–400) nanoseconds and frequency-converted IR lasers of diode laser, optically-pumped Alexandrite or Li:SAF lasers, where efficient nonlinear crystals (as shown in FIG. 2) may be used to convert the fundamental wavelength (770–880 nm) into its fourth-harmonic at the UV tunable wavelength of (193–220 nm) with energy of (0.01–5.0) mJ, repetition rate of (1–10,000) and pulse duration of (0.05–50) nanoseconds. Only two nonlinear crystals are needed in this case and overall efficiency is higher than that of the fifth harmonic generation which requires three nonlinear crystals. The basic laser may also include ultrashort pulsed lasers, such as a commercialized mode-locked Ti:sapphire laser or other solid-state laser, with wavelength ranges of (750–1100 nm), repetition rates of (0.01–100 MHz), energy per pulse of (0.01–100) microjoules, and pulse durations of (0.05–10) picoseconds where focused beam spot size of (0.05–0.5) mm is required to achieve the ablation threshold. When using an ultrashort pulse laser with very high peak power density (gigawatts range), the tissue ablation should be insensitive to laser wavelengths since the tissue ablation is assisted by the plasma-enhanced absorption with minimal tissue thermal damage. A focused spot size of (0.05–0.5) mm of the ultrashort pulsed lasers would be appropriate to achieve the tissue ablation and precise ablation profile is available by the scanning device proposed by the present invention. Without a scanning device, an ultrashort pulsed laser cannot be used in refractive surgery due to its energy level of less than 0.1 mJ and spot size smaller than 0.5 mm. The above-described lasers may also be frequency-converted into UV ranges of (190–220) nm suitable for photoablation.

The basic laser also includes a mid-IR (2.5–3.2 microns) laser generated from optical parametric oscillation (OPO) using a near-IR laser (such as Nd:YAG or Nd:YLF, flash-lamp or diode-pumped) as the pumping sources and KTP or BBO as the frequency conversion crystals. The OPO laser has advantages over the Q-switched Er:YAG laser, including higher repetition rate (10–5,000 Hz) and shorter pulse width (1–40 n.s.). These advantages provide faster surgical procedure and reduced thermal damage on the ablated corneal tissue. Typical energy per pulse of the OPO laser is (0.1–10) mJ. Greater detail on OPO was published by the inventor in Optical Communications, vol. 75, p. 315 (1990).

Still referring to FIG. 1, the scanning device 12 is synchronized with the laser repetition rate, where the computer software is capable of providing predetermined patterns according to a patient's corneal topography for the corrections of myopia, hyperopia and astigmatism. Astigmatic correction, in particular, is difficult to perform in prior art systems using a non-scanning diaphragm but can be easily achieved by the present invention using a scanning device. Furthermore, a multi-zone procedure for high diopter (6–15) changes can be performed by the computer program rather than that of the conventional mechanical iris.

The low-power laser systems described in the present invention can perform the procedures normally required in high-power lasers because a scanning device is used to assure the uniform corneal ablation by beam overlap and the ablation threshold is achievable by small spot size.

Referring to FIG. 2, a preferred embodiment for the basic laser 10 of FIG. 1 having a UV wavelength includes a diode-pumped Nd:YAG (or Nd:YLF) 25 having a fundamental wavelength of 1064 nm (or 1047 and 1053 nm) 26 and is focused by a lens 27 into a doubling crystal 28 (KTP, KNbO3, LBO or BBO) to generate a green wavelength 30 at 532 nm (or 524 and 527 nm). The green beam 30 is further converted by a fourth harmonic crystal 31 (BBO) to generate a UV wavelength 32 at 266 nm (or 262–263 nm) which is finally converted by a fifth harmonic crystal 33 to generate the UV wavelength 11 at 213 nm (or 209–211 nm). From a commercially available diode-pumped Nd:YLF laser I am able to achieve the UV (at 209–211 nm) energy of 0.01–2 mJ per pulse with average-power of 0.1 to 0.5 W. This energy level when focused into a spot size of (0.1–0.5) mm is sufficient to ablate the corneal tissue. This diode-pumped fifth-harmonic system provides the most compact refractive UV solid-state laser available today with the advantages of long lifetime, low maintenance, portability and absence of toxic gas in comparison with the excimer lasers currently used by other companies. Furthermore by using the fundamental wavelength at 1064 nm (or 1053 or 1047 nm) or their second-harmonic (at 532, 524, or 527 nm), intrastroma photokeratectomy procedure may be performed by focusing the beam into the intrastroma area of the cornea. The laser presented in the present invention provide a compact, portable and low-cost IPK laser and has an advantage over the lasers used by other companies where the systems are currently more than five times heavier and are more costly.

In FIG. 3, a commercially available Ho:YAG (or Er:glass) or diode laser 35 (either flash-lamp or laser-diode pumped) is coupled by a fiber optic waveguide 36 with core diameter of (100–600) microns to a scanning device 37, in which the fundamental beam 38 with a wavelength of 2.1 (or 1.54) or (1.9–2.5) microns which is collimated by a lens 40 and coupled to the scanning gavo 41 and focused by another lens 42 onto the beam splitters 43 and 44, and finally delivered to a target (such as a patient's cornea) 45. The IR (2.1 microns) laser beam 38 is collinear with the aiming beam 46 (visible He—Ne or diode laser) and the patent corneal center is also defined by a commercial slit-lamp microscope station 47. The above-described apparatus offers the unique feature of non-contact laser thermokeratoplasty for precise coagulation in both spherical and astigmatic corneal power corrections with scanning patterns predetermined by a computer software hereinafter discussed. The focusing lens 28 may be motorized for varying the focal point and thus varying the coagulation cone size for optimal results. In the prior art of fiber-tip contact system, the precision of the coagulation zone and patterns are limited by doctors manual operation which is a much slower procedure than the computer controlled scanning device described in the present invention. The requirement of replacing the fiber-tip after each operation is also a drawback of the prior art systems. The advantages of the present system includes: precision coagulation zone and spot size, flexible patterns for a variety of corrections, fast processing time and elimination of the need for fiber-tip replacement.

Still referring to FIG. 3, the basic laser 22 in accordance with the preferred embodiment of the present invention is a free-running or continuous-wave (CW) flash-lamp or diode-laser pumped Ho:YAG (at 2.1 microns) or Er:glass (at 1.54 microns), or IR diode laser (1.9–2.5 microns) with average power of 0.5–5 W, pulse duration of 200–2,000 microseconds (if free-running). In the present invention, the IR wavelengths of 1.54 and 2.1 and (1.9–2.5) microns are chosen due to their strong tissue absorption which is required in the photo-coagulation processes. Similar lasing media of Ho:Tm:YAG and Ho:Tm:Cr:YAG is also included in the preferred embodiments of the present invention. The CW diode laser (1.9–2.5 microns) may be scanned in a faster rate than that of the free-running lasers.

FIGS. 4A through 4E summarize the possible coagulation patterns suitable for both spherical and astigmatic corneal reshaping in the LTK procedures in a cornea 50. FIG. 4-A with coagulation zone (CZ) of 5 to 9 mm and spot number (SN) of (8–16) provides hyperopic corrections of 1–6 diopters; FIG. 4-B has a coagulation zone of 1–3 mm suitable for myopic corrections; FIG. 4-C has radial coagulation zone and spot number of 16–32, suitable for spherical hyperopic correction; FIG. 4-D has a coagulation zone of 1–9 mm and spot number of 50–200, suitable for precise coagulation control to stabilize and reinforce the collagen shrinkage tension; FIG. 4-E is designed for astigmatic change, where the coagulation patterns are chosen according to the corneal topography. By using the computer-controlled scanning, these patterns may be easily generated and predetermined according to the measured corneal topography of each patients. A combination of these patterns illustrated in FIGS. 4-A to 4-E enables the treatment of patent's optical power correction in all aspects of myopia, hyperopia, astigmatism and their mixed vision disorder. Furthermore, laser parameters such as energy per pulse, spot size and scanning patterns also provide another degree of freedom for the laser thermokeratoplasty process which are not usually available in the prior art systems using the contact fiber-tip.

The appropriate parameters relating to FIG. 4A–B are: laser energy per pulse of 5–50 mJ for free-running mode (200–400 micro-second duration), beam spot size of (0.1–1) mm, laser repetition rate of 5–30 Hz, coagulation zone of (1–10) mm, spot number of 8–200 spots and fiber core diameter of 100–600 microns, for a flash-lamp-pumped system. Also disclosed is the use of a diode-pumped Ho:YAG, either in a pulse-mode or continuous-wave (CW) mode. For a CW mode laser, energy of 10–100 mW is sufficient for coagulation when spot size of 0.05–0.5 mm is employed. In the diode-pumped system in CW mode or with a high-repetition-rate 20–100 Hz, a fast scanning enables completion of the coagulation procedures within 2–20 seconds depending upon the coagulation zone and spot number required. Fast scanning also provides a uniform collagen shrinkage unlike that of the prior art system using a manually operated fiber-tip which normally takes 1 to 5 minutes to complete in a multiple coagulation zone and high spot number. It is difficult to use a manually operated fiber-tip to generate the precise patterns as illustrated in FIG. 4 which can be easily performed in the computer-controlled scanning device as disclosed in the present invention. The patient's eye motion and decentration is a problem for prior art systems, but it is not a critical factor in the fast scanning device described herein.

Referring to FIG. 5, a laser-assisted myopic keratomileusis (MKM) and hyperopic keratomileusis (HKM) can be performed either on the outer corneal surface 51 or on the inner surface 52 to reshape the resealed corneal tissue without materially effecting the Bowman's layer. The preferred lasers are described in FIG. 1 including the UV (193–220 nm) and IR (2.5–3.2 microns) lasers. The non-invasive laser-assisted procedure disclosed in the present invention has the advantages over the procedures of photorefractive keratectomy and laser thermokeratoplasty including being safer, more stable with a higher diopter change, and without materially affecting epithelium and Bowman's layer. In comparison with the conventional keratomileusis, the laser-assisted myopic keratomileusis and hyperopic keratomileusis do not require corneal freezing and can perform very high diopter change not available by radial keratotomy or photorefractive keratectomy. Laser-assisted corneal preshaping can also be employed for a donor cornea in the procedure currently performed by epikeratophakia. Details of conventional lamellar refractive surgery may be found in Leo D. Bores, Refractive Eye Surgery (Blackwell Scientific Pub., 1993), Chapter 10.

FIGS. 6A through 6D shows a nearly flat-top beam profile achieved by overlapping a series of laser beams, where the degree of overlap, 50%–80%, depends on the individual beam profiles which are not required to be flat-top. In the present invention, the preferred individual beam profile is either a 70% Gaussian or a symmetric profile. In the laboratory, I have demonstrated a smooth laser-ablated PMMA surface with zone diameter of 3–6 mm by overlapping a large number of pulses, 500 to 5,000, each one having a spot size of 0.8–1.2 mm. Moreover smooth transition among the ablation zones were achieved without the transition zone steps found in prior art systems using mechanical diaphragms. In addition to the myopic and hyperopic scanning patterns of 6B and 6C, one of the significant features of the present scanning device is that it can generate predetermined patterns based upon the corneal topography for astigmatism correction (see 6D). Corneal scar may also be easily located by a topography and photoablated by a laser based on the computer-controlled scanning patterns. The preferred lasers for the procedures described in FIG. 6 are discussed in connection with FIG. 1.

Still referring to FIG. 6, the scanning schemes were tested by ablation on PMMA plasty. The computer software is based upon the mathematical model described earlier in equations 1 and 2 where the center ablation thickness was equally spaced to define the associate scanning diameters. Given the ablation thickness per pulse and per ablation layer (at a given scanning diameter), one may easily obtain the overall corneal surface ablation profile, (see equation (1)). The number of required ablation layers is therefore proportional to the diopter change (D) and square of the ablation zone (W). The computer parameters designed in the present invention include: diopter change (D), optical zone diameter (W), and the degrees of overlap in both tangential (TD) and radial (RD) direction of the scan patterns as shown in FIGS. 6A through 6D. Smooth PMMA surface ablation was achieved by optimization of laser spot size, energy and the overlap parameters of TD and RD. Experimental data indicates that larger overlap provides smoother surface ablation, however, longer ablation time is required for a given diopter change, laser energy and repetition rate (RR). Larger RR, 50–100 Hz, provides shorter ablation time which is typically in the range of (20–40) seconds for diopter changes of 2–8 in myopic treatment based upon my measurements. The prior art high-power excimer lasers with a typical RR of 5–15 Hz will be impossible to achieve the results described above even if they use the present scanning device.

Still referring to FIGS. 6, using the UV lasers (193, 210 and 213 nm) I have achieved ablation depths of (20–40) microns by overlapping (2000–4000) laser pulses, which give an ablation depth of 0.05–0.1 microns per pulse. The ablation depths are measured by 1a microsensor (made by Tencor Instruments) which has a resolution of about 0.5 microns or better. Ablation curves, ablation depth versus laser intensity, were obtained by varying the laser energy or the spot size. Given the ablation rate (ablation thickness per pulse), I am able to calibrate the number of pulses and the degree of beam overlap required to achieve the diopter change on the PMMA, where the diopters of the ablated PMMA are measured by the standard lensmeter. In vitro measurement of corneal tissue ablation can be calibrated according to the comparison of the ablation rate between PMMA and tissue. For myopic and hyperopic corrections, I have used circular scanning patterns with beam overlap controlled by the tangential scanning speed and diameters of the adjoined circles. The preferred scanning scheme is from small circle to large circle. For example, given a laser spot size of 1 mm, a radial overlap of 50% will require the scanning circle to start from 1 mm diameter to 5 mm diameters with an increment of 0.5 mm for an optical zone of 5 mm. Furthermore, a tangential overlap of 50% requires the scanner to move at an angular speed of about 23 degrees within the interval between each laser pulse. In my computer-controlled scanning device, software was developed to synchronize the laser repetition rate with the scanning gavo to control the above-described overlap patterns. In addition to the circular patterns described for myopic and hyperopic treatments, a linear scanning pattern may also be used in particular for the myoptic and astigmatic corrections.

It is important to note that a uniform individual beam profile and energy stability of the laser, under the present scanning device, are not critical in achieving an overall uniform ablation zone whereas they are very critical for prior art systems using expanding iris devices. Given the ablation rate per overlapped circle, the overall diopter correction may be achieved by the appropriate increment in diameters of the expanding circles. Greater details of beam scanning and overlapping will be further discussed in connection with FIGS. 9–11.

Referring to FIGS. 7A and 7B, a laser radial keratectomy (LRK) performed by laser excision has advantages over the conventional diamond-knife radial keratotomy (RK) including higher predictability and reproducibility by precise control of the excision (or ablation) depth. Furthermore, using the scanning device of the present invention, laser radial keratotomy may be performed easily and rapidly with less dependance upon the surgeon's skill and experience. Corneal reshaping may be performed by controlling the laser parameters such as spot size, intensity, scanning speed, beam overlap, and the excision depth per pulse which typically ranges from 0.2 to 0.5 microns. The excision depth precision of a laser is at least 10 times better than that of a knife. This "laser-knife" should be able to perform all the radial keratotomy procedures performed by a "diamond-knife" by using similar techniques to those introduced in the Book of Leo D. Bores, Refractive Eye Surgery, Chapters 8 and 9. Examples of laser radial keratotomy are shown in 7A for myopia (radial-cut) and 7B for astigmatism (T-cut). The preferred lasers for laser radial keratotomy include the lasers described in FIG. 1.

Figure 8B:
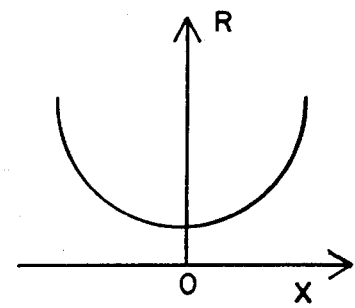
Figure 8C:
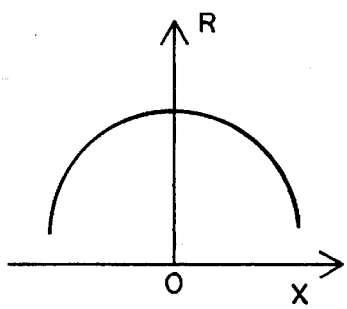
Figure 8D:
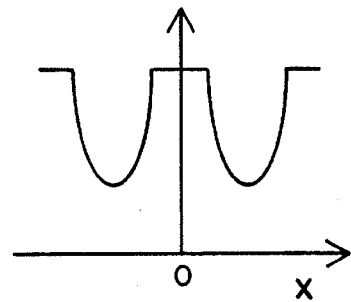

Referring to FIGS. 8A and 8D, the ablation patterns suitable for refractive procedures may be generated by using coated windows such as UV (or IR) grade fused silica, MgF, BaF or sapphire (when an IR laser is used), with preferred thickness of (0.5–2) mm and diameter of (8–15) mm. Referring to FIG. 8A, scanning laser beams 53 (at wavelength of UV or IR) with circular scanning pattern to deliver uniform (or constant) laser energy over the coated window 44 with coating specification (at UV or IR wavelength) according to the profile on the corneal tissue 55 (or PMMA surface) will also achieve the same pattern described by equation (1). FIGS. 8B and 8C show the reflection profiles of the coated windows for myopia, hyperopia and astigmatism, respectively, based on predetermined diopter changes. These coated windows disclosed in the present invention can be reused for cost effectiveness and has an advantage over the prior art system using the disposable mask which is costly and is difficult to provide reproducible results due to the non-uniform transmission or ablation properties of the mask.

Greater detail of the features of the present invention regarding beam overlap, scanning and orientation in order to achieve uniform ablation profiles to meet the clinical requirements of corneal reshaping are demonstrated as follows. The actually measured PMMA profiles were generated from the Microsensor (made by TENCOR INSTRUMENTS, INC.) using our ArF laser (the Compak-200 Mini-Excimer system, made by LaserSight, Inc.) having laser parameters of: (2–4 mJ) energy at the output window, operated at (50–200) Hz, with the beam focused onto the corneal surface at a spot size of about (0.2–1.2) mm, with energy per pulse of (0.5–1.5) mJ, tunable by a coated MgF window.

Figure 9A:
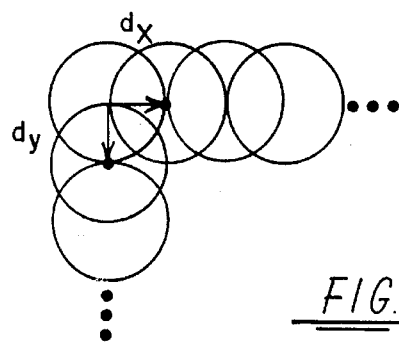
FIGS. 9A through 9B show the spatial overlap for uniform pattern.

Referring to FIG. 9A, we show the schematic of the motion of the scanning beam with a spot size of 1 mm in this example. Beam overlap function(L) is defined by the beam displacement parameters of dx and dy (in x and y direction, respectively, on the corneal plane) adjustable by the computer controlled software, where $Lx=1-dx/R$ and $Ly=1-dy/R$, where R is the beam diameter. The degrees of smoothness (DS) of the ablated PMMA surface (a plastic sheet which has been commonly used for the calibration of UV laser ablation on corneal tissue) is governed by the degrees of overlap function $L=Lx+Ly$. Greater DS can be performed by using greater L, which, however, will also cause a slower procedure speed (v), at a given laser average-power(p), beam spot size(R) and energy per pulse (E). Desired procedure time of 20 to 50 seconds are typical for patient diopter corrections (myopic) of $D=-3$ to $-10$, where patient centration is conducted by a visible fixation light for the patient to look at without eye movement. Including some of the compensation from the recovered epithelium filling on the ablated corneal surface, the roughness of the corneal tissue, calibrated by the PMMA surface, should be within the range of (0.2–2) microns. Therefore, we are optimizing the parameters of dx, dy, L,p, E and R in order to achieve the above-described clinical requirements.

Figure 9B:
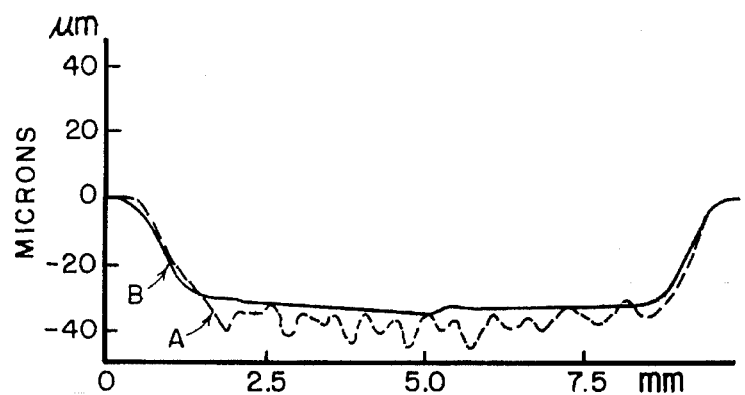

Referring to FIG. 9B, a comparison is shown to demonstrate the degrees of smoothness of the ablated PMMA at two sets of displacements: curve A (dx=dy=0.5 m) and curve B(dx=0.5 mm, dy=0.3 mm). These PMMA profiles were generated from a Microsensor scanned along the y direction to show the difference in smoothness caused by the difference in dy values (at a fixed dx value). It is clearly demonstrated by comparing Curves A and B that a smoother surface is generated with a smaller displacement (dy=0.3 mm), or larger beam overlap Lx=70%. In this particular example, the basic beam profile is worse than a 50% Gaussian and actually has a three-lop structure which is typical in an ArF excimer laser. Even under this poor beam uniformity condition, we are still able to obtain very uniform overall ablated areas of (2–9) mm in diameter, as shown in FIG. 9B (curve B) with surface roughness less than 1 microns (vs. about 10 microns in curve A), when a set of appropriate beam overlap parameters are used. Smaller dx and dy will further improve smoothness, which, however, may take a longer operation time. As shown in above example (using dx=0.5 mm and dy=0.3 mm), only 30 seconds is needed for a D=–4 diopter correction with enough smoothness of the PMMA surface, where I used a pulse energy of 0.9 mJ (on the PMMA surface), with the system operated at 100 Hz in this example.

Figure 10A:
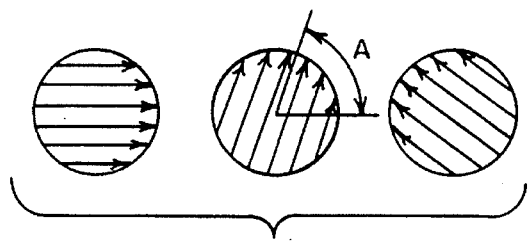
FIGS. 10A through 10B show the beam orientation for smooth ablation.
Figure 10B:
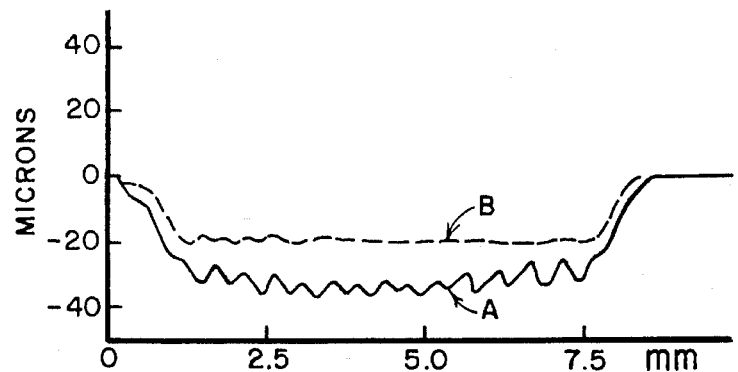

In addition to the overlap function, I have been able to further improve the beam uniformity by the beam orientation method as follows. As shown in FIG. 10A, I used linear scan patterns for multi-layer ablation on a PMMA sheet, where parameters of E=0.9 mJ, spot size of 1 mm, dx=dy= 0.5 mm were used. In one case, I repeated the linear scan pattern along the x-direction, or rotation angle (A)=zero, for about 25 times (layers). To see the improvement due to pattern orientation, I tried the second case by rotating the linear-scan angle (A) by about 65 degrees in each successive scan layers. An angle A=65 degrees was chosen in this particular example to randomize the basic beam structure (having a non-uniform profile) and to achieve the uniform overall ablation. This averaging procedure by beam orientation will largely reduce the potential roughness caused by the basic beam structure, noting that rotation angles, such as 20, 30, 60 or 120 degrees (in which 360 degrees can be divided into integers), should be avoided to prevent repeated patterns after a few rotation layers. A larger angle(A) is chosen for smaller diopter corrections and vice versa for the best results. This is to make sure that enough beam randomization is performed for various diopter corrections which are proportional to the numbers of scanned layers. Comparisons are shown in FIG. 10B for A=0 (nonrotated case, curve A) and for A=65 (rotated case, curve B), where dx=dy=0.5 mm were used in both cases. Significant smoothness of ablated PMMA was achieved in the rotated case (curve B) even when a large displacement of dy=0.5 mm was used, compared to curve B in FIG. 10B and curve A in FIG. 9B. The larger displacement, or smaller overlap results in a faster procedure, however, this results in a loss of smoothness if beam rotation is not used. Using the above-described techniques, I am able to generate the predetermined ablation profiles corresponding to various refractive corrections such as myopic, hyperopic and astigmatic with clinically acceptable tissue smoothness and procedures times requirement.

Figure 11A:
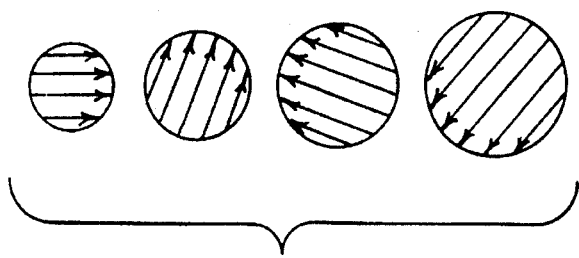
FIG. 11 shows the oriented expanding scanning to achieve the required ablation profiles, where the diameters are governed by a mathematical formula.
Figure 11B:
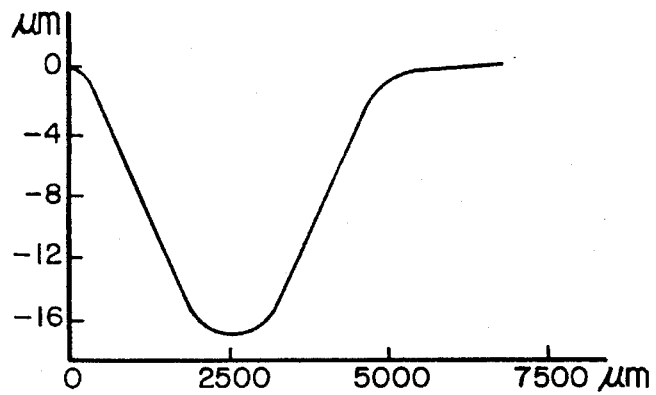

Referring to FIG. 11, an example for myopic correction is shown. FIG. 11A shows the schematic of rotated ablated areas with increasing diameters (from about 0.5 to 6 mm) governed by Equation (1), where a typical number of layers (or scanned areas at various diameters) of 25 is needed for a −5 diopter correction. For an optical zone of 5 mm, this represents an ablation rate of about 2 microns in corneal tissue in each layer, where a pulse energy of about 0.9 mJ at spot size of 1 mm and repetition rate of 100 Hz is used. For smaller diopter corrections, a smaller energy (0.6–0.8 mJ), or smaller ablation rate (0.5–1.0 microns) is desired for smoother and more accurate results. Moreover, a smaller spot size of (0.1–0.5 mm) may be used for better control of the ablation profile (with greater accuracy), but a faster laser repetition rate larger than 500 Hz would be required for a reasonable procedure speed of (20–50) seconds to cover (−3 to −10) diopter corrections. In this situation the diode pumped UV solid state laser described earlier will be a better candidate than the Excimer laser. FIG. 11B shows the PMMA ablation profile measured from a Microsensor using the techniques shown in FIG. 11A, where an ablation zone size of about 5 mm with center depth of about 16 microns were shown. I believe that the PMMA profiles shown in FIGS. 9 through 11 represent, for the first time, the novel features of the techniques disclosed in the present invention. Some of the prior art has never demonstrated the actual ablation data, although a simple concept of beam scanning has been proposed. The comparisons in FIGS. 9 and 10 have demonstrated that the prior techniques as set forth in the background hereto would never achieve the smooth surface as shown here. In addition, given the laser parameters proposed in the present invention of low-energy (2–4 mJ) with nonuniform basic beam profile and without using mechanical beam re-shaping, it is impossible for the prior art to achieve clinically meaningful results. A high-power laser of 100–300 mJ with a complex means of beam uniformity is always required in the prior art patents.

The method disclosed in the present invention combines beam scanning, overlapping and pattern rotation (randomization) provides a powerful yet simple technique for optimal results of laser refractive surgery which involves both clinical aspects (ablation diopter, ablation optical zone, smoothness, patient centration and operation speed) and engineering aspects (beam profile, uniformity, stability, energy, spot size and delivery systems).

It is worth emphasizing that the concept of achieving a smooth ablation surface by using the randomly rotated scanning pattern as disclosed in the present invention would not be demonstrated if the microsensor were not used to measure the PMMA profiles. I have preformed hundreds of PMMA profile analyses at various laser parameters together with the theoretical model presented in equations (1)–(5) are the key factors behind the present process. Furthermore, the refractive correction profile, governed by equation (1) would be very difficult to justify after the scanning method is applied to the target (PMMA and corneal tissue) if the microsensor is not available to the user. The PMMA data presented in the present invention have also been employed on corneas, where hundreds of patient's have been treated by the Compak-200, Mini-Excimer with predictable power corrections and smooth tissue ablation. Clinical results are to be presented in optthalmology conferences.

While the invention has been shown and described with reference to the preferred embodiments thereof, it will be understood by those skilled in the art that the foregoing and other changes and variations in form and detail may be made therein without departing from the spirit, scope and teaching to the invention. Accordingly, the method and apparatus, the ophthalmic applications herein disclosed are to be considered merely as illustrative and the invention is to be limited only as set forth in the claims.

I claim:

1. A method of performing corneal refractive surgery by reshaping a portion of a corneal surface comprising the steps of:

selecting a laser having a pulsed output beam of predetermined ultraviolet wavelength and having an energy level less than 10 mJ/pulse;

selecting a scanning mechanism for scanning said selected laser output beam, said scanning mechanism including a galvanometer scanning mechanism for controlling said laser beam into an overlapping pattern of adjacent pulses;

coupling said laser beam to a scanning device for scanning said laser beam over a predetermined surface;

focusing said scanning laser beam onto a corneal surface to a predetermined generally fixed spot size;

aligning the center of the said scanning laser beam onto the corneal surface with a visible aiming beam;

controlling the scanning mechanism to deliver the scanning laser beam in a predetermined overlapping pattern onto a plurality of positions on the corneal surface to photoablate or photocoagulate corneal tissue; and removing from 0.05 to 0.5 microns of corneal tissue per pulse overlapped to remove tissue to a desired depth, whereby a patient's vision is corrected by the reshaping of the corneal surface of the patient's eye using a low power laser.

2. A method of performing corneal refractive surgery by reshaping a portion of the corneal surface in accordance with claim 1 in which the step of selecting a laser includes selecting a diode-pumped UV laser having an output wavelength between 193 and 220 nanometers, and energy per pulse of 0.01 to 5 mJ/pulse, a repetition rate of between 1 Hz and 10 KHz, and a pulse duration between 0.1 picoseconds to 50 nanoseconds and a focused spot size of (0.05–1.5) mm on the corneal surface.

3. A method of performing corneal refractive surgery by reshaping a portion of the corneal surface in accordance with claim 1 in which the step of selecting a laser includes selecting a flash lamp pumped UV laser having an output wavelength between 193 and 220 nanometers, and energy per pulse of 0.1 to 10 mJ/pulse, a repetition rate of between 1 Hz and 10 KHz, and a pulse duration between 0.1 picoseconds to 50 nanoseconds and a focused spot size of (0.05–1.5) mm on the corneal surface.

4. A method of performing corneal refractive surgery by reshaping a portion of the corneal surface in accordance with claim 1 in which the step of selecting a laser includes selecting an argon fluoride excimer laser having an output wavelength of 193 nanometers, energy per pulse of 0.5 to 10 mJ/pulse and a focused generally fixed spot size of between 0.2 to 2 mm on the corneal surface, and a repetition rate of between 1 to 1,000 Hz, and pulse duration of between 1 to 50 nanoseconds.

5. A method of performing corneal refractive surgery by reshaping a portion of the corneal surface in accordance with claim 1 in which the step of selecting a laser includes selecting a free-running Ho:YAG laser having an output wavelength of about 2.1 microns at an average power of between 0.5–5 watts and a focused generally fixed spot size of between 0.1–1 mm.

6. A method of performing corneal refractive surgery by reshaping a portion of the corneal surface in accordance with claim 1 in which the step of selecting a laser includes selecting a free-running Er:glass laser having an output wavelength of about 1.54 microns at an average power of between 0.5–5 watts with a focused generally fixed spot size of between 0.1–1 mm.

7. A method of performing corneal refractive surgery by reshaping a portion of the corneal surface in accordance with claim 1 in which the step of selecting a laser includes selecting a free-running Er:glass laser having an output wavelength of between 1.9 to 2.5 microns at a power of between 0.5–5 watts and a focused generally fixed spot size of between 0.1–1 mm.

8. A method of performing corneal refractive surgery by reshaping a portion of the corneal surface in accordance with claim 1 in which the step of selecting a laser includes selecting a Q-switched Er:YAG laser having an output wavelength of 2.94 microns, and a pulse duration of between 50 to 400 nanoseconds, with an energy per pulse of between 50– 500 mJ and a repetition rate of between 1 and 200 Hz with a focused generally fixed spot size of between 0.2–2 mm.

9. A method of performing corneal refractive surgery by reshaping a portion of the corneal surface in accordance with claim 1 in which the step of selecting a laser includes selecting an ultra-short pulsed laser having an output wavelength of between 750 to 1100 nanometers, energy per pulse of between 0.01 to 100 microjoules, and a repetition rate of between 0.01 to 100 MHz, and pulse duration of between 0.05–10 picoseconds and a focused generally fixed spot size of between 0.05–0.5 mm.

10. A method of performing corneal refractive surgery by reshaping a portion of the corneal surface in accordance with claim 1 in which the step of selecting a laser includes selecting an OPO mid-IR laser having an output of 2.5–3.2 microns, a pulse duration of between 1–40 nanoseconds and energy per pulse of between 0.1 to 10 mJ, and a repetition rate of between 10 and 5,000 Hz and a focused generally fixed spot size on the corneal surface of between 0.1–2 mm.

11. A method of performing corneal refractive surgery by reshaping a portion of the corneal surface in accordance with claim 1 in which the step of delivering said laser beam includes said focusing lens which is highly transparent to the said laser beam, said focusing lens having a focal length of (50–1500) mm for focusing the laser source onto a generally fixed spot size of 0.05–2 mm on a predetermined position on the corneal surface.

12. A method of performing corneal refractive surgery by reshaping a portion of the corneal surface in accordance with claim 1 in which the step of controlling said scanning mechanism includes controlling said scanning to scan a pattern of radial aligned spots using a laser beam capable of photocoagulation corneal tissue.

13. A method of performing corneal refractive surgery by reshaping a portion of the corneal surface in accordance with claim 1 in which the step of controlling said scanning mechanism includes controlling said scanning to scan a pattern of concentric generally fixed spots using a laser beam capable of photocoagulating corneal tissue.

14. A method of performing corneal refractive surgery by reshaping a portion of the corneal surface in accordance with claim 1 in which the step of controlling said scanning device includes controlling said scanning to scan a pattern of generally fixed area ring spots using a laser beam capable of photocoagulating corneal tissues.

15. A method of performing corneal refractive surgery by reshaping a portion of the corneal surface in accordance with claim 1 in which the step of controlling said scanning device includes controlling said scanning to scan a pattern of overlapping generally fixed ring spots using a laser beam capable of photoablating corneal tissue for myopic correction.

16. A method of performing corneal refractive surgery by reshaping a portion of the corneal surface in accordance with claim 1 in which the step of controlling said scanning mechanism includes controlling said scanning to scan a pattern of overlapping generally fixed area spots using a laser beam capable of photoablating the corneal tissue for hyperopic correction.

17. A method of performing corneal refractive surgery by reshaping a portion of the corneal surface in accordance with claim 1 in which the step of controlling said scanning mechanism includes controlling said scanning to scan a pattern of overlapping circles of fixed area using a laser beam capable of photoablating the corneal tissue for astigmatic correction.

18. A method of performing corneal refractive surgery by reshaping a portion of the corneal surface in accordance with claim 1 in which the step of controlling said scanning mechanism includes controlling said scanning to scan a pattern of radial aligned slits of fixed area using a laser beam capable of photoablating corneal tissue for laser radial keratectomy.

19. A method of performing corneal refractive surgery by reshaping a portion of the corneal surface in accordance with claim 18 wherein the step of scanning includes scanning a coated window having a predetermined coating to direct said laser beam therethrough and to photoablate the corneal surface to meet a predetermined profile for refractive corrections.

20. A method of performing corneal refractive surgery by reshaping a portion of the corneal surface in accordance with claim 18 in which the step of scanning includes scanning through a coated window made of materials transparent to a UV laser having an output beam of (193–215) nm.

21. A method of performing corneal refractive surgery by reshaping a portion of the corneal surface in accordance with claim 18 in which the step of scanning includes scanning through a coated window made of materials highly transparent to an IR laser having an output beam of (2.5–3.2) microns.

22. A method of performing corneal refractive surgery by reshaping a portion of the corneal surface in accordance with claim 1 in which the step of controlling said scanning mechanism includes controlling said scanning which has a circular scanning pattern to deliver uniform laser energy over a coated window positioning near the corneal surface.

23. A method of performing corneal refractive surgery by reshaping a portion of the corneal surface in accordance with claim 1 including the step of scanning in a uniform scanned pattern with a spatial overlap of 50–80% and beam orientation whereby the initial beam profile uniformity is not critical.

* * * * *